(12) United States Patent
Jacobson et al.

(10) Patent No.: US 8,258,354 B2
(45) Date of Patent: Sep. 4, 2012

(54) PRODUCING SHORT CHAIN PERFLUOROALKYL IODIDES

(75) Inventors: Stephen Ernest Jacobson, Hockessin, DE (US); Sourav Kumar Sengupta, Wilmington, DE (US); John Joseph Hagedorn, Newark, DE (US); Liza Lopez, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 309 days.

(21) Appl. No.: 12/796,020

(22) Filed: Jun. 8, 2010

(65) Prior Publication Data

US 2011/0301390 A1    Dec. 8, 2011

(51) Int. Cl.
*C07C 17/361* (2006.01)
*C07C 17/26* (2006.01)
*C07C 19/08* (2006.01)

(52) U.S. Cl. .................... 570/218; 570/237; 570/134

(58) Field of Classification Search .................. 570/134, 570/218, 237
See application file for complete search history.

(56) References Cited

U.S. PATENT DOCUMENTS

| | | | |
|---|---|---|---|
| 3,132,185 A | 5/1964 | Parsons | |
| 3,234,294 A | 2/1966 | Parsons | |
| 5,268,516 A | 12/1993 | Bertocchio et al. | |

FOREIGN PATENT DOCUMENTS

| | | |
|---|---|---|
| DE | 4410551 A1 | 9/1995 |
| FR | 1380555 | 10/1963 |
| GB | 1283348 | 7/1972 |
| JP | 2009143812 A | 7/2009 |

OTHER PUBLICATIONS

Hauptschein, Murray et al.; Transformation of Polyfluoroalkyl Iodides, The Organic Research Department, Pennsylvania Salt Manufacturing Co.; Mar. 14, 1957; pp. 6248-6253; vol. 79.
Grygorcewicz, C. et al.; The Exchange Reaction of Pentafluoroethyl Iodide with Iodine; The Journal of Physical Chemistry; May 1968; pp. 1811-1812; vol. 72, No. 5.
Probst, Anton et al., Thermolysis and UV-Photolysis of Perfluorinated Iodo-Alkanes and Iodo-Oxaalkanes: There is a Preferred Reaction Channel; Journal of Fluorine Chemistry; May 30, 1989; pp. 163-173; vol. 47 (1990); Elsevier Sequoia/Printed in The Netherlands.
Skorobogatov, G. A., et al.; Rate and Equilibrium Constants for RI . dblarw. R + i and l + RI dblarw; Nllnst., Khim., Leningrad, USSR; Zhurnal Obshchei Khimii (1991), 61(1), pp. 178-185.

*Primary Examiner* — Jafar Parsa

(57) ABSTRACT

An improved process for producing perfluoroalkyl iodides of formula (I)

$$F(CF_2CF_2)_n-I \quad (I)$$

wherein n is an integer from 2 to 3, wherein the improvement comprises contacting at least one perfluoroalkyl iodide of formula (II) and at least one perfluoroalkyl iodide of formula (III)

$$F(CF_2CF_2)_m-I \quad (II)$$

$$F(CF_2CF_2)_p-I \quad (III)$$

wherein m is an integer greater than or equal to 3, and p is an integer equal to or lower than 2, at a) a molar ratio of formula (III) to formula (II) of from about 1:1 to about 6:1, b) a residence time of from about 1 to about 9 seconds, and c) a temperature of from about 450° C. to about 495° C.

9 Claims, No Drawings

PRODUCING SHORT CHAIN PERFLUOROALKYL IODIDES

BACKGROUND OF THE INVENTION

Long chain perfluoroalkyl iodides are prepared by the conventional telomerization of pentafluoroethyl iodide with tetrafluoroethylene (TFE). This telomerization yields perfluoroalkyl iodides with a polymer distribution of varying TFE insertions. Most current processes produce chain lengths from 8 carbons to 20 carbons in length. Perfluoroalkyl iodides have many uses as a key starting material in the preparation of surface modifying products, such as repellants, stain and soil resist agents, as well as surfactants. The current trend in these end use markets is the use of fluorine efficient molecules. Fluorine efficient molecules are those molecules that contain a shorter chain perfluoroalkyl component. To produce these fluorine efficient molecules, shorter chain perfluoroalkyl iodides are needed as starting materials.

Bertocchio et al., in U.S. Pat. No. 5,268,516, claims a process for preparation of shorter chain perfluoroalkyl iodides in a thermal telomerization of TFE with pentafluoroethyl iodide or heptafluoroisopropyl iodide by adjusting feed concentration and location of the TFE. This process is distinct in that it is a telomerization of TFE.

Becker et al., in German Patent Application DE 4,410,551A1, disclose a process for preparing short chain perfluoroalkyl iodides by reaction of longer chain perfluoroalkyl iodides (greater than 8 carbons in the perfluoroalkyl) with shorter chain perfluoroalkyl iodides (6 carbons or less in the perfluoroalkyl) to produce the desired short chain perfluoroalkyl iodides as well as inert perfluoroalkanes as a by-product. Becker et al., added iodine in the process to increase selectivity of the perfluoroalkyl iodide over the perfluoroalkanes, but it has been found that this also decreased the yield of the perfluoroalkyl iodides. The addition of iodine ($I_2$) increases the presence of water into the system, potentially producing a second inert by product, hydro-end capped fluoroalkanes.

The use of iodine causes several issues in processes. Iodine introduces opportunities for line plugs, a need for iodine recycling and neutralization, and the potential hydrogen iodide formation. Iodine could also introduce water contamination into the process leading to production of unwanted inert by-products, hydro-end capped fluoroalkanes.

There is a need for a process for the production of shorter chain perfluoroalkyl iodides, that has high yields, high selectivity, and is free of the use of iodine as a reactant. The present invention meets these needs.

SUMMARY OF THE INVENTION

The present invention provides an improved process for producing perfluoroalkyl iodides of formula (I)

$$F(CF_2CF_2)_n\text{—}I \quad (I)$$

wherein n is an integer from 2 to 3, wherein the improvement comprises contacting at least one perfluoroalkyl iodide of formula (II) and at least one perfluoroalkyl iodide of formula (III)

$$F(CF_2CF_2)_m\text{—}I \quad (II)$$

$$F(CF_2CF_2)_p\text{—}I \quad (III)$$

wherein m is an integer greater than or equal to 3, and p is an integer equal to or lower than 2, at a) a molar ratio of formula (III) to formula (II) of from about 1:1 to about 6:1, b) a residence time of from about 1 to about 9 seconds, and c) a temperature of from about 450° C. to about 495° C.

DETAILED DESCRIPTION

Herein trademarks are shown in upper case.

The term "perfluoroalkyl iodides" refers to fully fluorinated alkyl chains with an iodine on the terminal carbon represented by the generic formula $F(CF_2CF_2)_d\text{—}I$ wherein d is 1 to about 10. The term "perfluoroalkanes" refers to fully fluorinated alkyl chains represented by the generic formula $F(CF_2CF_2)_d\text{—}F$ wherein d is 2 to about 20. The term "hydro-end capped fluoroalkanes" refers to fluorinated alkyl chains represented by the generic formula $F(CF_2CF_2)_d\text{—}H$ wherein d is 1 to about 10.

The present invention comprises an improved process for producing perfluoroalkyl iodides of formula (I)

$$F(CF_2CF_2)_n\text{—}I \quad (I)$$

wherein n is an integer from 2 to 3, wherein the improvement comprises contacting at least one perfluoroalkyl iodide of formula (II) and at least one perfluoroalkyl iodide of formula (III)

$$F(CF_2CF_2)_m\text{—}I \quad (II)$$

$$F(CF_2CF_2)_p\text{—}I \quad (III)$$

wherein m is an integer greater than or equal to 3, preferably m is an integer greater than or equal to 4, and p is an integer equal to or lower than 2, preferably p is 1, at a) a molar ratio of formula (III) to formula (II) of from about 1:1 to about 6:1, b) a residence time of from about 1 to about 9 seconds, and c) a temperature of from about 450° C. to about 495° C.

The present invention provides for converting the undesirable longer chain perfluoroalkyl iodides of formula (II) by contacting with the shorter perfluoroalkyl iodides of formula (III) (perfluoroethyl iodide, perfluorobutyl iodide, or mixtures thereof), at reaction conditions as defined above, to produce desired perfluoroalkyl iodides of formula (I), as shown in reaction scheme 1.

Reaction Scheme 1:

$$F(CF_2CF_2)_4\text{—}I + \text{excess } F(CF_2CF_2)\text{—}I \rightarrow F(CF_2CF_2)_2\text{—}I + F(CF_2CF_2)_3\text{—}I$$

The present invention also selectively limits the formation of perfluoroalkanes and higher homologue perfluoroalkyl iodides where the perfluoroalkyl group in the perfluoroalkyl iodides has 10 carbons or more. Perfluoroalkanes are produced when two perfluoroalkyl iodides react with each other, as shown in reaction scheme 2.

Reaction Scheme 2:

$$F(CF_2CF_2)_4\text{—}I + F(CF_2CF_2)_4\text{—}I \rightarrow F(CF_2CF_2)_4\text{—}(CF_2CF_2)_4F + I_2$$

It is understood that this reaction to form a perfluoroalkane is not limited to compounds of formula (II) and can occur with any perfluoroalkyl iodides present in the process as a reactant or a product. Higher and lower homologues of perfluoroalkyl iodides can also be produced by the reaction of perfluoroalkyl iodides reactants of formula (II) as shown in reaction scheme 3.

Reaction Scheme 3:

$$F(CF_2CF_2)_4\text{—}I + F(CF_2CF_2)_4\text{—}I \rightarrow F(CF_2CF_2)_6\text{—}I + F(CF_2CF_2)_2\text{—}I$$

It is understood that this reaction to form higher and lower homologue perfluoroalkyl iodides is not limited to use of compounds of formula (II) as the reactant. The reaction to form products which are higher or lower homologue perfluoroalkyl iodides can occur using any perfluoroalkyl iodides present in the process as reactants.

The reactant compounds of formula (II) are commercially available from E. I. du Pont de Nemours and Company, Wilmington, Del. or can be produced according to a telomerization process as described in U.S. Pat. Nos. 3,234,294 and 3,132,185, each herein incorporated by reference. Compounds of formula (III), pentafluoroethyl iodide, can be purchased from Sigma-Aldrich, St. Louis, Mo.

The present invention is carried out by passing liquid or gas streams of compounds of formula (II) and liquid or gas streams of formula (III) through a heated reactor. The streams can be diluted with an inert gas, such as nitrogen. The reactor can be a stand alone process, or can be coupled to the end of a telomerization process to produce compounds of formula (I). The present invention can also be conducted as a batch process in addition to a continuous feed process. The reactants are typically pumped through tubing, such as stainless steel, preferably to a preheater. The reactants are employed in a molar ratio of formula (III) to formula (II) of from about 1:1 to about 6:1. The reactants are preheated to a temperature of from about 200° C. to about 350° C. The reactants are thoroughly mixed using conventional equipment, such as a static mixer. Additional heating can be employed during mixing. The mixture is then conducted through a reactor wherein it is heated to a temperature of from about 450° C. to about 495° C. The residence time in the reactor is from about 1 to about 9 seconds. The product stream exiting the reactor is then cooled and transferred to containers for storage or distribution. The product stream, including any byproducts and unreacted materials can be recycled back into the process without isolation to improve efficiency.

Preferably, the ratio of the reactant compounds of formula (III) to formula (II) is from about 2:1 to from about 6:1, more preferably from about 2:1 to about 4:1. The residence time of the reactants in the reactor is preferably from about 2 to about 8 seconds, more preferably from about from about 4 to about 6 seconds, and more preferably from about 4 to about 5 seconds. The reaction preferably is conducted at temperatures of from about 470° C. to about 495° C., more preferably at about 480° C. to about 490° C.; and more preferably at about 490° C. When using a temperature that is lower within the above cited range, a longer residence time can be employed, such as, up to 30 seconds. At higher temperatures within or above the above cited range a residence time of less than one second can be employed.

The present invention is useful in increasing both yield and selectivity for formula (I) without use of iodine ($I_2$) as a reactant. An increase in yield and selectivity is accomplished while also minimizing the formation of perfluoroalkanes (byproduct). Iodine use tends to decrease the yield and also could cause the formation of hydro-end capped fluoroalkanes, which is avoided in the process of the present invention. Iodine also can cause line plugging due to iodine condensation, and introduces the need for recycling or neutralizing the unreacted iodine. In the process of the present invention the selectivity is a minimum of 50 mole % without the addition of iodine as a reactant, preferably the minimum is 55 mole %, more preferably the minimum is 60 mole %, while maintaining a yield of at least 30%, typically at least 33%, or preferably at least 35%, or higher, without the use of iodine as a reactant. The amount of perfluoroalkane and higher homologue perfluoroalkyl iodides obtained using the process of the present invention is a maximum of about 45 mole %, wherein the perfluoroalkyl group in the higher homologue perfluoroalkyl iodides has 10 or more carbons, preferably a maximum of about 42 mole %, and more preferably a maximum of about 40 mole %, or even more preferably 35 mole % without the use of iodine as a reactant, and while obtaining a yield of at least 30 mole % or higher, preferably about 33% or higher.

The increased yield and selectivity of the process of the present invention are both useful in generating commercial quantities of the shorter chain perfluoroalkyl iodides economically for use as starting materials in the preparation of surface modifying products. Increased yield decreases production time by decreasing the number of passes needed to convert longer chain perfluoroalkyl iodides into compounds of formula (I). Increased selectivity results in a larger amount of desirable perfluoroalkyl iodides of formula (I) compared to the higher homologue perfluoroalkyl iodides, wherein the higher homologue perfluoroalkyl iodides have 10 or more carbons and perfluoroalkanes. Hydro-end capped fluoroalkanes were not detected in the present invention. Perfluoroalkanes and hydro-end capped fluoroalkanes are inert and cannot be used as starting materials to produce surface modifying products.

The process of the present invention provides perfluoroalkyl iodides of formula (I) containing four and six carbons in the perfluoroalkyl chain. This is beneficial for use in producing surface modifying products containing the corresponding short perfluoroalkyl chains, which is desired for fluorine efficiency in such products. Fluorine is costly, so use of less fluorine provides more economical products.

MATERIALS AND TEST METHODS

Perfluorooctyl iodide is commercially available as ZONYL Tel AOP from E. I. du Pont de Nemours and Company, Wilmington, Del. Pentafluoroethyl iodide and iodine are commercially available from Sigma-Aldrich, St. Louis, Mo.

Analysis of the products was carried out by gas chromatography equipped with a flame ionization detector (GC-FID) and results are given in molar %, unless otherwise noted. The samples were treated with sodium bisulfite to reduce and neutralize iodine.

EXAMPLES

Example 1

Perfluorooctyl iodide and pentafluoroethyl iodide were pumped through stainless steel tubing (⅛") and combined into one stream, which was passed through a preheater at 215° C. For Example 1 the ratio of perfluorooctyl iodide and pentafluoroethyl iodide (mole %), reaction temperature (° C.), and residence time (RT) in seconds are listed in Table 1. The mixture then flowed into a reactor (INCONEL 600, ¼") set at 450° C. The reactor length and/or the flow rate of the reactants were varied to allow for the desired residence time. A sample was taken and analyzed by GC-FID. The stream was then cooled to 215° C. and transferred into a storage tank. Yield and selectivity data are also listed in Table 1. Yield was based on total moles of $F(CF_2CF_2)_2$—I and $F(CF_2CF_2)_3$—I produced times the conversion of $F(CF_2CF_2)_4$—I entering the reaction, and is expressed as a percent. Selectivity was based on the total moles of $F(CF_2CF_2)_2$—I and $F(CF_2CF_2)_3$—I compared to the total moles of $F(CF_2CF_2)_{5+}$—I and perfluoroalkanes produced.

Examples 2 to 8

Examples 2 to 8 were conducted using the process of Example 1 and the ratios of perfluorooctyl iodide and pentafluoroethyl iodide (mole %), reaction temperatures (° C.), and residence times (RT) in seconds as listed in Table 1. The reactants were mixed and preheated, and the resulting mixture was then flowed into the reactor as described in Example 1, and was processed as described in Example 1. Yield and selectivity data are listed in Table 1.

Comparative Examples A-C

Comparative Examples A-C were conducted using the process of Example 1 except that iodine was used as an additional reactant. The ratios of perfluorooctyl iodide and pentafluoroethyl iodide (mole %), reaction temperatures (° C.), amounts of iodine (mole % based on total moles of perfluorooctyl iodide and pentafluoroethyl iodide), and residence times (RT) in seconds are listed in Table 1. The iodine was pumped through tubing (INCONEL 600, 1/8") and preheated to 215° C. The iodine stream was then mixed with the perfluorooctyl iodide and pentafluoroethyl iodide stream, thoroughly mixed with static mixers and heated to 300° C. The mixture was then flowed into the reactor as described in Example 1, and was processed as described in Example 1. Yield and selectivity data are listed in Table 1. For Comparative Examples A and C, conducted at 470° C. and 490° C. respectively, the use of the iodine increased selectivity, but decreased the yield. Comparative Example B using a longer residence time in the reactor resulted in a higher conversion but decreased selectivity, despite using higher amounts of iodine.

Comparative Examples D and E

Comparative Examples D and E were conducted using the process of Example 1 except that for Comparative Example D a high ratio of formula (III) to formula (II) was employed, and for Comparative Example E, a high temperature was employed. The ratios of perfluorooctyl iodide and pentafluoroethyl iodide (mole %), reaction temperatures (° C.), and residence times (RT) in seconds are listed in Table 1. The reactants were processed as in Example 1. Yield and selectivity data are listed in Table 1. For both Comparative Examples D and E lower selectivity was obtained with a higher level of byproducts.

From Table 1, the Examples of the present invention produced both high yield and high selectivity for $F(CF_2CF_2)_n$—I where n is 2 or 3. The Comparative Example A showed that the addition of iodine caused an increase in selectivity but also decreased overall yield of the desired products compared to the Examples 2 to 5 of the invention. Comparative Example C showed this same effect at a higher temperature versus Examples 6 to 8. Comparative Example B using a longer residence time in the reactor resulted in a higher conversion but decreased selectivity despite using higher amounts of iodine. Comparative Example D demonstrated that a high ratio of formula (III) to formula (II) can result in a high level of perfluoroalkane by-products while making a lower concentration of the higher perfluoroalkyl iodides ($F(CF_2CF_2)_{5+}$—I) compared to the Examples 6 to 8 of the invention. Comparative Example E, conducted at a higher temperature, demonstrated less selectivity than Examples 6 to 8 and generated a higher level of perfluoroalkanes than Examples 6 to 8.

What is claimed is:

1. An improved process for producing perfluoroalkyl iodides of formula (I)

$$F(CF_2CF_2)_n\text{—I} \qquad (I)$$

wherein n is an integer from 2 to 3, wherein the improvement comprises contacting at least one perfluoroalkyl iodide of formula (II) and at least one perfluoroalkyl iodide formula (III)

$$F(CF_2CF_2)_m\text{—I} \qquad (II)$$

$$F(CF_2CF_2)_p\text{—I} \qquad (III)$$

wherein m is an integer greater than or equal to 3, and p is an integer equal to or lower than 2, at a) a molar ratio of formula (III) to formula (II) of from about 1:1 to about 6:1, b) a residence time of from about 1 to about 9 seconds, and c) a temperature of from about 450° C. to about 495° C.

2. The process of claim 1, wherein the ratio of formula (III) to formula (II) is from about 2:1 to about 6:1.

3. The process of claim 1, wherein the temperature is from about 470° C. to about 490° C.

TABLE 1

| Run | Temp. (° C.) | Reaction Time (sec) | Molar ratio of $F(CF_2CF_2)_1$—I to $F(CF_2CF_2)_4$—I | Iodine (mole %) | Conversion of $F(CF_2CF_2)_4$—I (mole %) | Selectivity $F(CF_2CF_2)_2$—I + $F(CF_2CF_2)_3$—I (mole %) | $F(CF_2CF_2)_{5+}$—I + Perfluoro-alkanes (mole %) | $F(CF_2CF_2)_{5+}$—I (mole %) | Perfluoro-alkanes (mole %) | Yield (%) |
|---|---|---|---|---|---|---|---|---|---|---|
| 1 | 450 | 8.4 | 4.44 |  | 46 | 72 | 28 | 7 | 21 | 33 |
| 2 | 470 | 4.2 | 1.11 |  | 57 | 57 | 42 | 20 | 22 | 33 |
| 3 | 470 | 4.2 | 2.22 |  | 63 | 62 | 38 | 13 | 25 | 39 |
| 4 | 470 | 2.1 | 4.44 |  | 46 | 72 | 28 | 7 | 21 | 33 |
| 5 | 470 | 4.2 | 4.44 |  | 61 | 64 | 35 | 7 | 28 | 39 |
| Comp. A | 470 | 4.2 | 4.44 | 0.1 | 43 | 72 | 28 | 8 | 20 | 30 |
| 6 | 490 | 4.2 | 1.11 |  | 80 | 58 | 41 | 14 | 27 | 47 |
| 7 | 490 | 4.2 | 2.22 |  | 84 | 59 | 41 | 7 | 34 | 49 |
| Comp B | 490 | 18.9 | 2.22 | 0.5 | 99 | 44 | 56 | 7 | 49 | 44 |
| 8 | 490 | 4.2 | 4.44 |  | 82 | 63 | 37 | 4 | 33 | 52 |
| Comp C | 490 | 4.2 | 4.44 | 0.35 | 46 | 72 | 28 | 10 | 18 | 33 |
| Comp D | 490 | 4.2 | 17.76 |  | 86 | 35 | 65 | 1 | 64 | 30 |
| Comp E | 510 | 4.2 | 4.44 |  | 95 | 45 | 55 | 2 | 53 | 42 |

4. The process of claim 1, wherein the residence time is held at from about 4 to about 5 seconds.

5. The process of claim 1, wherein selectivity is for formula (I) without use of iodine as a reactant.

6. The process of claim 5 wherein the selectivity is a minimum of 50 mole % without addition of iodine as a reactant.

7. The process of claim 6 wherein the yield is at least 30%.

8. The process of claim 7 wherein the perfluoroalkanes and perfluoroalkyl iodides are a maximum of 45% wherein the perfluoroalkyl group in the perfluoroalkyl iodides has 10 or more carbons.

9. The process of claim 1, where p is 1 and m is an integer equal to or greater than 4.

* * * * *